United States Patent [19]

Petersen et al.

[11] Patent Number: 5,364,403
[45] Date of Patent: Nov. 15, 1994

[54] ACETABULAR CUP POSITIONER

[75] Inventors: Thomas D. Petersen, San Diego, Calif.; Richard A. Lane, Ft. Wayne, Ind.

[73] Assignee: Zimmer, Inc., Warsaw, Ind.

[21] Appl. No.: 123,240

[22] Filed: Sep. 20, 1993

[51] Int. Cl.5 ................................. A61F 2/34
[52] U.S. Cl. ........................................ 606/91
[58] Field of Search ................ 606/91, 99, 86, 89

[56] References Cited

U.S. PATENT DOCUMENTS

| D. 331,461 | 12/1992 | Lester | D24/140 |
| D. 340,979 | 11/1993 | Hershberger et al. | D24/133 |
| 3,859,992 | 1/1975 | Amstutz | |
| 4,305,394 | 12/1981 | Bertuch, Jr. | |
| 4,475,549 | 10/1984 | Oh | |
| 4,632,111 | 12/1986 | Roche | |
| 4,716,894 | 1/1988 | Lazzeri et al. | |
| 4,987,904 | 1/1991 | Wilson | 606/86 |
| 4,994,064 | 2/1991 | Aboczky | 606/91 |
| 5,037,424 | 8/1991 | Aboczsky | 606/91 |
| 5,061,270 | 10/1991 | Aboczky | 606/91 |
| 5,098,437 | 3/1992 | Kashuba et al. | 606/89 |
| 5,100,267 | 3/1992 | Salyer | 407/54 |
| 5,116,339 | 5/1992 | Glock | 606/91 |
| 5,169,399 | 12/1992 | Ryland et al. | 606/91 |
| 5,171,243 | 12/1992 | Kashuba et al. | 606/86 |
| 5,171,312 | 12/1992 | Salyer | 606/81 |
| 5,236,433 | 8/1993 | Salyer | 606/91 |
| 5,250,051 | 10/1993 | Maryan | 606/91 |

Primary Examiner—Tamara L. Graysay
Attorney, Agent, or Firm—Todd A. Dawson

[57] ABSTRACT

The acetabular cup positioner of this invention provides a resilient collar to be carried on its distal end for contacting the interior surface of the acetabular cup. The resilient collar prevents damage to the interior of the cup during impaction. Since the resilient collar will compress a small amount during the impaction, the threaded connector of the positioner and the threads for the acetabular cup will be under a sizable load. Therefore, to protect the positioner and the cup, the threaded connector is shiftably connected to the positioner body. The connector is biased toward the distal end by a helical spring.

4 Claims, 4 Drawing Sheets

ACETABULAR CUP POSITIONER

FIELD OF THE INVENTION

This invention relates to acetabular cup positioners as used in the total hip arthroplasty and has specific relevance to a cup positioner having a shiftable connecting shaft and cushioned distal end for the protection of a acetabular shell component.

BACKGROUND OF THE INVENTION

Acetabular cup positioners are used during total hip arthroplasty to assist the surgeon in positioning the prosthetic acetabular cup within the prepared acetabulum of the patient. Typically, the prosthetic cup will include a threaded central opening for accommodating a threaded stud of the cup positioner. To properly seat the acetabular cup within the prepared acetabulum of the patient, the surgeon will impact the proximal end of the cup positioner. If the distal end of the cup positioner is in contact with the interior surface of the cup, this impaction may cause a slight gouge or imperfection in the cup.

SUMMARY OF THE INVENTION

The acetabular cup positioner of this invention provides a resilient collar to be carried on its distal end for contacting the interior surface of the acetabular cup. The resilient collar prevents damage to the interior of the cup during impaction. Since the resilient collar will compress a small amount during the impaction, the threaded connector of the positioner and the threads for the acetabular cup will be under a sizable load. Therefore, to protect the positioner and the cup, the threaded connector is shiftably connected to the positioner body. The connector is biased toward the distal end by a helical spring.

Accordingly, it is an object of the invention to provide for a novel prosthetic acetabular cup positioner.

Another object of the invention is to provide for a novel cup positioner with a resilient collar on its distal end.

Another object of the invention is to provide for a novel cup positioner having shiftable threaded connector biased toward the distal end of the positioner by a spring.

Other objects of the invention will become apparent upon a reading of the following description taken with the accompanying drawings.

DESCRIPTION OF THE PREFERRED EMBODIMENTS

The preferred embodiments herein described are not intended to be exhaustive nor to limit the invention to the precise forms disclosed. Rather, they are chosen and described to best explain the invention so that others skilled in the art might utilize their teachings.

Figure 1:
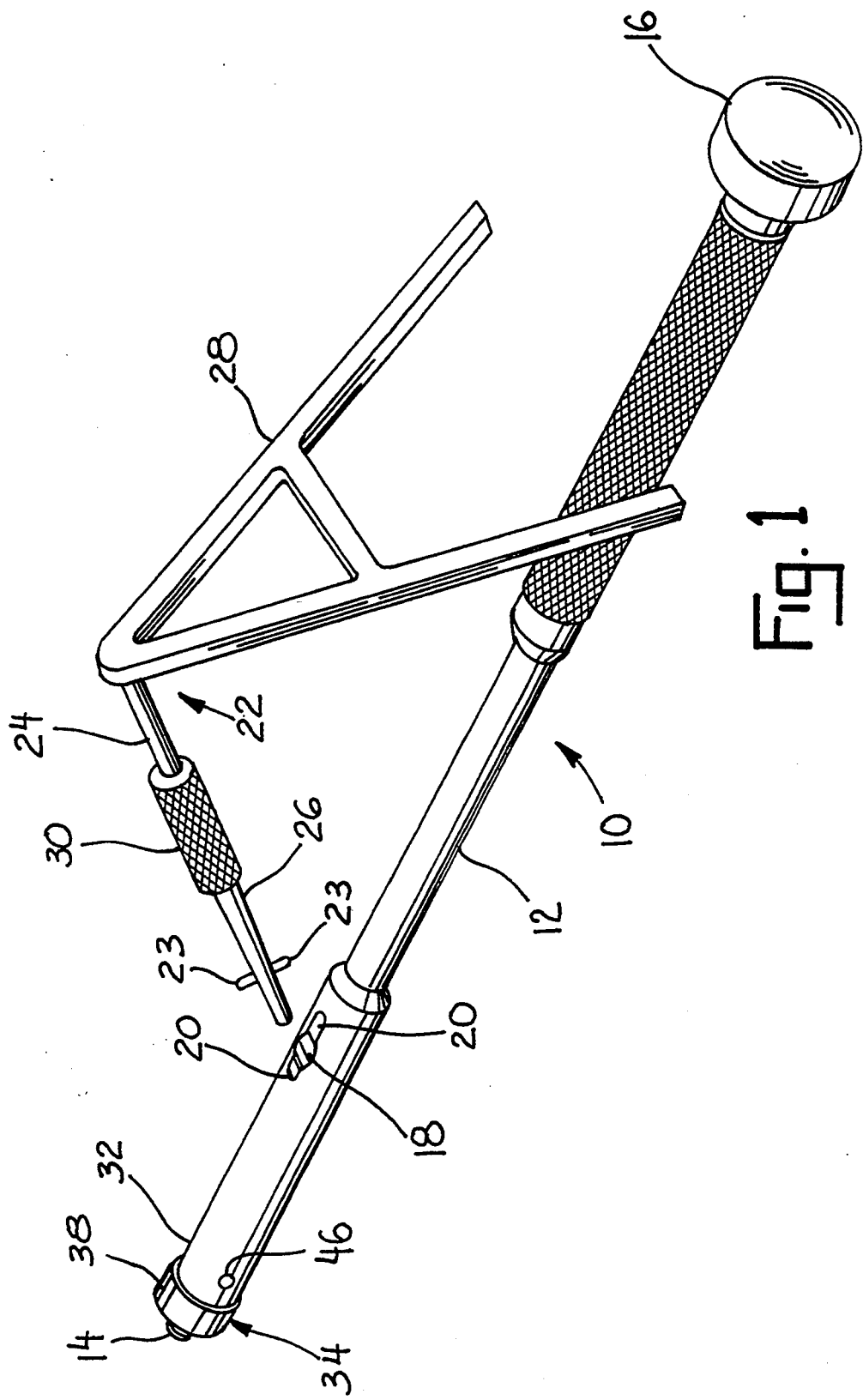
FIG. 1 is a perspective view of the acetabular cup positioner of the invention, its sighting guide disconnected from the positioned shaft.
Figure 2:
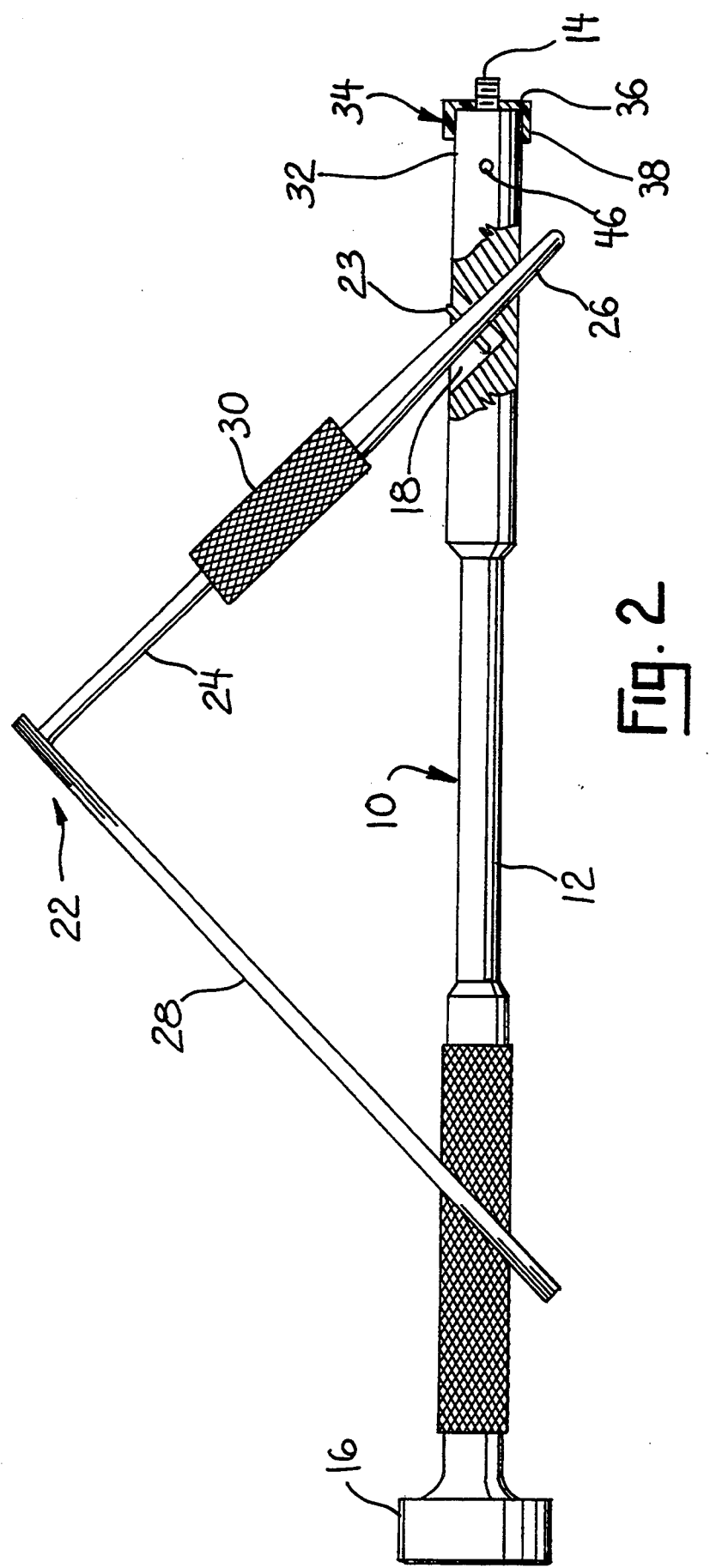
FIG. 2 is an elevational view of the invention with portions cut away for illustrative purposes.

Referring now to the drawings, prosthetic acetabular cup positioner 10 (hereinafter positioner 10) includes a main shaft 12 having a threaded stud 14 extending longitudinally out one end and a head 16 connected to an opposite end. Threaded stud 14 is configured for turning within a threaded central bore of a prosthetic acetabular cup 8 (see FIGS. 4 and 5) as is well known in the industry. Threaded stud 14 is shiftably carried by shaft 12 as will be explained in detail below. Head 16 provides an impact surface as is also well known in the art. A tapered through bore 18 is formed in shaft 12 at an angle as illustrated in FIG. 2. A pair of key ways 20 are formed in shaft 12 in communication with through bore 18.

Sighting guide 22 includes a generally cylindrical shaft 24 terminating in a tapered distal end 26. A shoulder 25 is formed at the junction of tapered distal end 26 and the generally cylindrical shaft of sighting guide 22. A pair of alignment pins 23 extend generally transversely from the tapered distal end of the sighting guide. The opposite end of guide 22 is connected to an A-shaped alignment guide 28. A-shaped alignment guide 28 provides a means for the surgeon to visually check the alignment of the acetabular cup with anatomical check points on the patient as is well know in the art. A cylindrical slaphammer mechanism 30 having a central bore is carried on the cylindrical shaft 24 of sighting guide 22 and is shiftable between a first position adjacent the shoulder 25 and a second position adjacent sighting guide 22. Slaphammer 30 is a generally solid cylinder of metal with the central bore formed therethrough.

Figure 3:
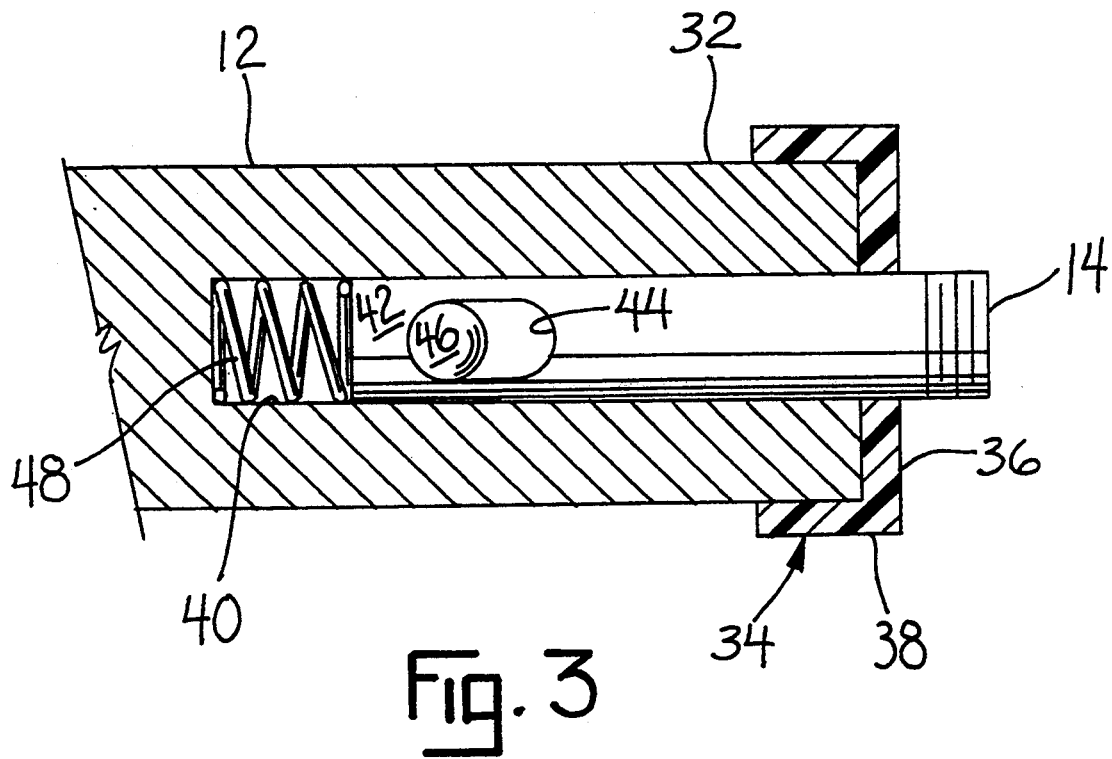
FIG. 3 is an enlarged cross-sectional view of the distal end of the cup positioner of the invention.
Figure 4:
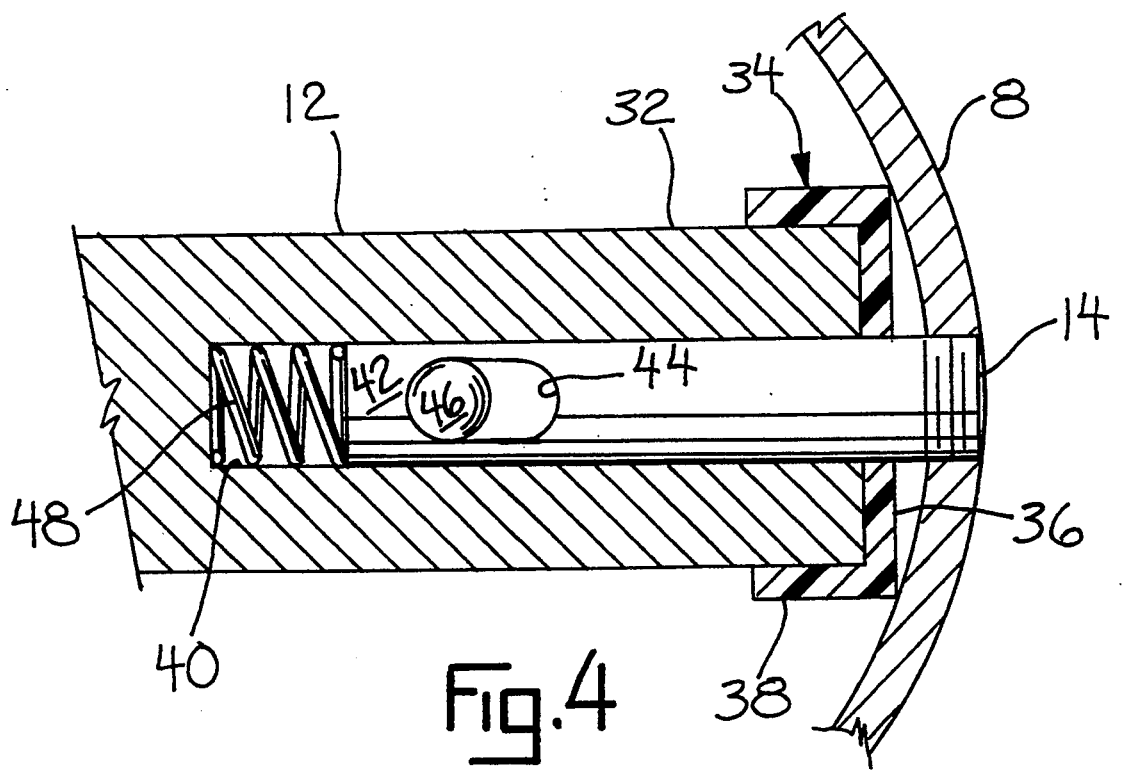
FIG. 4 is the view of FIG. 3 illustrating an acetabular cup connected to the positioner.
Figure 5:
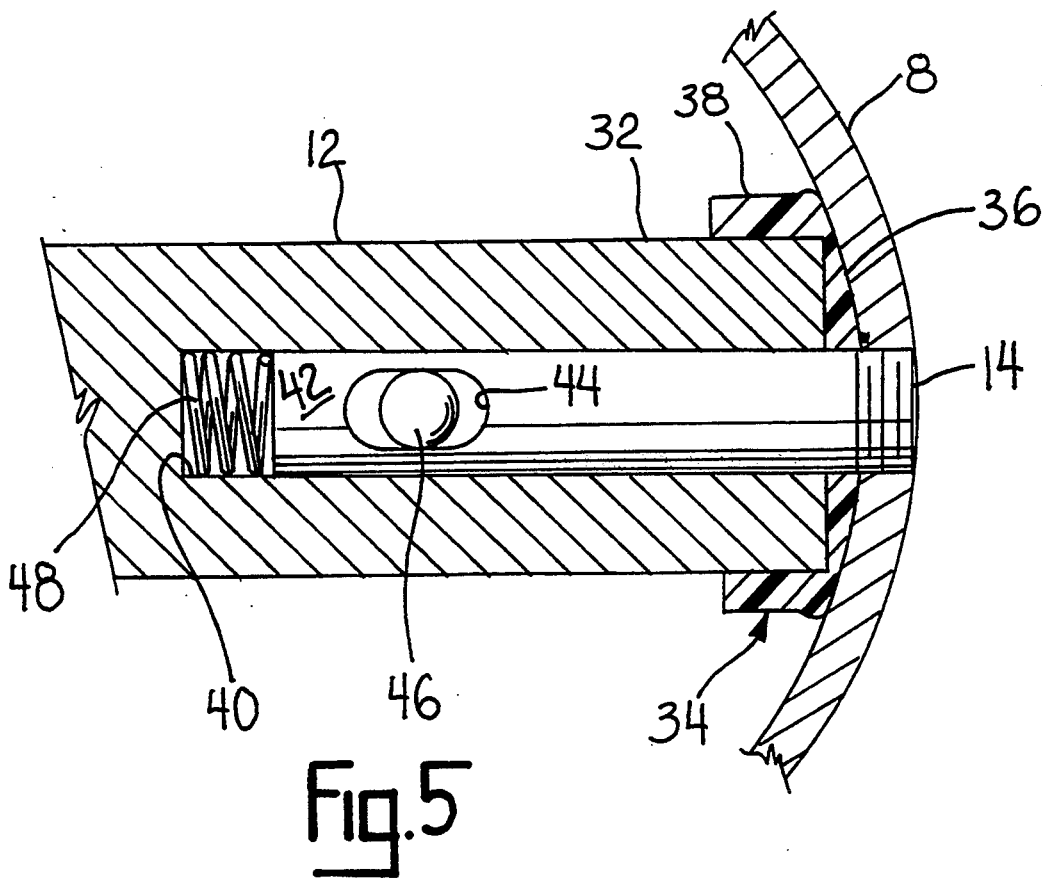
FIG. 5 is the view of FIG. 4 during impaction of the acetabular cup.

As illustrated in FIGS. 3 through 5, the distal end 32 of shaft 12 is covered by a collar 34 having an end wall 36 and an integral side wall 38. Collar 34 is frictionally retained on shaft 12 and is formed from a resilient material. Collar 34 includes a central opening through end wall 36 to accommodate threaded stud 14.

The distal end 32 of shaft 12 includes a central blind bore 40 extending longitudinally within the shaft as illustrated in FIGS. 3 through 6. Threaded stud 14 is accommodated within the bore 40. Stud 14 includes a threaded end which extends outwardly from shaft 12. A slot 44 is formed through stud 14 adjacent non-threaded end 42. A pin 46 extends through the distal end of shaft 12 and slot 44 to retain stud 14 within shaft 12. A helical spring 48 is positioned between non-threaded end 42 and the end wall of blind bore 40 to bias the stud into the position of FIG. 3. Stud 14 may be urged into bore 40 upon pressure being applied to the stud in a longitudinal direction toward the proximal end of the shaft. Stud 14 may be shifted between a first position illustrated in FIG. 3 and a second position wherein the pin would engage the opposite end of slot 44.

In use, the surgeon rotates an acetabular cup onto the stud 14 of shaft 12 and inserts the tapered distal end 26 of sighting guide 22 into the tapered through bore 18 such that alignment pins 23 are accommodated within the key ways 20 formed adjacent the throughbore. The surgeon may gently tap the sighting guide to securely engage the tapered distal end 26 and tapered bore 18 in a tight fit. The tapered distal end and tapered bore configuration for mating two components is well known in the art and is generally referred to as a Morse Taper. The cup 8 is rotated onto the threaded stud until the interior of the cup firmly contacts the collar 34.

Once the surgeon has properly sighted the acetabular cup relative to the patients anatomical landmarks, the acetabular cup is impacted into place within the acetabulum. The surgeon impacts handle 16. The force of the impact causes the collar to momentarily compress between the interior surface of the acetabular cup and the distal end of shaft 12. As the collar is compressed, threaded stud 14 is shifted from its extended position of FIG. 4 an amount equal to the compression of collar 34. As illustrated in FIG. 5, the retraction of stud 14 protects the threads of stud 14 and of the acetabular cup. The collar 34 protects the interior surface of the acetabular cup 8 during impaction.

Once the surgeon has properly impacted the acetabular cup into the prepared acetabulum of the patient, the cup positioner needs to be rotated off of the cup. However, with sighting guide 22 attached, such rotation is impossible. Therefore, to remove the sighting guide 22, the surgeon grasps the slaphammer mechanism 30 and briskly slides the slaphammer into repeated contact with the A-shaped guide 28 until the tapered distal end disengages from the tapered bore. Once the sighting guide is removed, the surgeon may easily rotate the main shaft 12 relative to the acetabular cup for removal therefrom.

Figure 6:
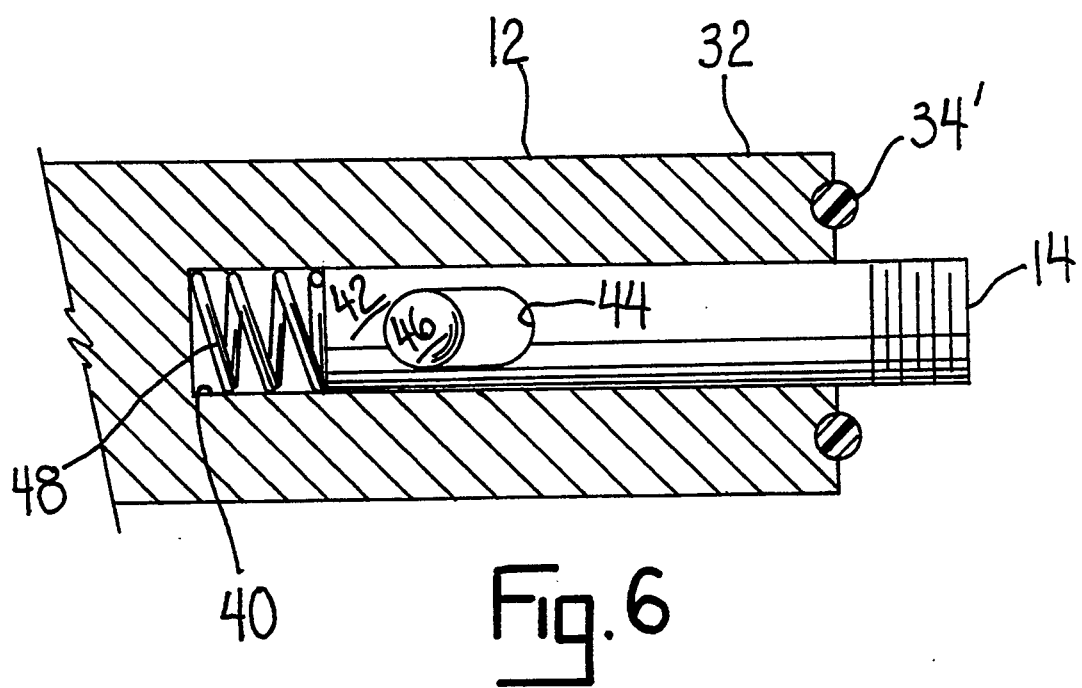
FIG. 6 is an alternative embodiment of the acetabular cup positioner of the invention.

An alternative embodiment of the invention is illustrated in FIG. 6. In the embodiment of FIG. 6, collar 34 has been substituted for by an O-ring 34' which is partially seated into the distal end of shaft 12 as illustrated. The O-ring functions in a similar manner to the collar 34 of FIGS. 3–5 as well as the threaded stud 14.

Further it should be understood that the invention is not to be limited by the precise form disclosed but may be modified within the keeping of the appended claims.

We claim:

1. A positioner configured for connection to a prosthetic acetabular cup, said positioner including a main shaft having a means for connecting the positioner to a prosthetic acetabular cup, said connecting means being shiftable from an extended position toward a retracted position in response to the shaft being impacted toward an acetabular cup carried by the connecting means, wherein said shaft carries a resilient collar adjacent the connecting means, the collar being configured for contact with the acetabular cup, the connecting means includes a partially threaded stud positioned within a longitudinal cavity formed in a distal end of the shaft, a spring member positioned between an end wall of the longitudinal cavity and the threaded stud so as to bias the stud outwardly from the cavity toward the extended position.

2. The cup position of claim 1 wherein said stud includes a slot formed therein, a pin being accommodated within the slot and connected to the stud to retain the shaft within the cavity.

3. The cup positioner of claim 2 wherein said collar includes an integral end wall and side wall, said side wall extending about the periphery of the shaft adjacent said connecting means, said end wall including an opening for accommodating the connecting means.

4. An acetabular cup positioner configured for impacting an acetabular cup against a prepared surface, said acetabular cup including an interior surface and a threaded central bore, the positioner including a longitudinal shaft having a proximal end having a head forming an impaction surface and a distal end configured to engage the acetabular cup, the distal end including a resilient member for compressive engagement between the interior surface of the acetabular cup and the distal end of the shaft, the resilient member comprising means for preventing damage to the interior surface of the acetabular cup, said distal end includes a connecting means carried by the shaft and being shiftable from an extended position toward a retracted position in response to the positioner being impacted against the cup and the resilient member compressing, the connecting means including a stud configured for threaded engagement within the threaded central bore of the cup, said stud positioned within a cavity formed in said shaft and being biased into said extended position by a spring member.

* * * * *